US010363278B2

(12) United States Patent
Beaudry et al.

(10) Patent No.: US 10,363,278 B2
(45) Date of Patent: Jul. 30, 2019

(54) FROZEN THERAPEUTIC DOSE AND PACKAGE

(71) Applicant: Amnio Technology LLC, Phoenix, AZ (US)

(72) Inventors: Christian Beaudry, Phoenix, AZ (US); Terrell Suddarth, Winchester, TN (US); Bruce Werber, Phoenix, AZ (US)

(73) Assignee: Amnio Technology LLC, Phoenix, AZ (US)

( * ) Notice: Subject to any disclaimer, the term of this patent is extended or adjusted under 35 U.S.C. 154(b) by 13 days.

(21) Appl. No.: 15/381,044

(22) Filed: Dec. 15, 2016

(65) Prior Publication Data

US 2017/0095515 A1 Apr. 6, 2017

Related U.S. Application Data

(63) Continuation-in-part of application No. PCT/US2015/035749, filed on Jun. 15, 2015, which
(Continued)

(51) Int. Cl.
*A61K 35/50* (2015.01)
*A61F 9/00* (2006.01)
(Continued)

(52) U.S. Cl.
CPC ............ *A61K 35/50* (2013.01); *A61F 9/0008* (2013.01); *A61J 1/14* (2013.01); *A61K 8/982* (2013.01); *A61K 9/14* (2013.01); *A61K 35/28* (2013.01); *A61K 35/35* (2013.01); *A61K 35/44* (2013.01); *A61K 35/545* (2013.01); *A61K 47/20* (2013.01); *A61K 47/46* (2013.01); *A61M 5/178* (2013.01);
(Continued)

(58) Field of Classification Search
CPC ...................................................... A61K 35/50
See application file for complete search history.

(56) References Cited

U.S. PATENT DOCUMENTS 6,153,292 A 11/2000 Bell et al.
7,871,646 B2 1/2011 Ghinelli
(Continued)

OTHER PUBLICATIONS

Abdulrazzak et al, Current Stem Cell Research & Therapy, 2013, vol. 8, pp. 117-124. (Year: 2013).*

*Primary Examiner* — Allison M Fox
(74) *Attorney, Agent, or Firm* — Alex Hobson

(57) ABSTRACT

A frozen therapeutic dose includes an amniotic material and is configured into a pack for easy administering of the dose to a treatment location. A frozen therapeutic dose may contain a concentration of live amniotic stem cells. A frozen therapeutic dose may be provided in a form, such as a multi-pack form, to enable a person to administer a dose to a treatment location without the need of traveling to a doctor's office or clinic. A frozen therapeutic dose package may be kept in a conventional freezer at −20° C. for example, for extended periods of time and a person may remove the package as needed for treatment. A frozen dose package or pack may contain a secondary material configured to mix with the frozen therapeutic dose. A secondary material may be configured within a single dose compartment with the frozen dose or within a separate compartment.

16 Claims, 14 Drawing Sheets

Related U.S. Application Data is a continuation-in-part of application No. PCT/US2015/035746, filed on Jun. 15, 2015, and a continuation-in-part of application No. 14/853,889, filed on Sep. 14, 2015, now Pat. No. 9,814,746, which is a continuation-in-part of application No. 14/593,415, filed on Jan. 9, 2015, now Pat. No. 9,132,156, said application No. 14/853,889 is a continuation-in-part of application No. PCT/US2015/019294, filed on Mar. 6, 2015, and a continuation-in-part of application No. PCT/US2015/019318, filed on Mar. 6, 2015, and a continuation-in-part of application No. PCT/US2015/019311, filed on Mar. 6, 2015.

(60) Provisional application No. 62/012,396, filed on Jun. 15, 2014, provisional application No. 62/012,394, filed on Jun. 15, 2014.

(51) Int. Cl.

| | | |
|---|---|---|
| *A61J 1/14* | (2006.01) | |
| *A61K 8/98* | (2006.01) | |
| *A61K 9/14* | (2006.01) | |
| *A61K 35/28* | (2015.01) | |
| *A61K 35/35* | (2015.01) | |
| *A61K 35/44* | (2015.01) | |
| *A61K 47/20* | (2006.01) | |
| *A61K 47/46* | (2006.01) | |
| *A61M 11/00* | (2006.01) | |
| *A61M 5/178* | (2006.01) | |
| *A61Q 19/08* | (2006.01) | |
| *C12N 5/073* | (2010.01) | |
| *A61K 35/545* | (2015.01) | |

(52) U.S. Cl.
CPC .......... *A61M 11/00* (2013.01); *A61Q 19/08* (2013.01); *C12N 5/0605* (2013.01); *A61J 2200/44* (2013.01)

(56) References Cited

U.S. PATENT DOCUMENTS

| | | |
|---|---|---|
| 8,540,970 B2 | 9/2013 | Rodriguez-Vilaboa |
| 8,672,879 B2 | 3/2014 | Grant et al. |
| 8,932,805 B1 * | 1/2015 | Brahm ............... C12N 5/0605 435/1.3 |
| 2004/0048796 A1 | 3/2004 | Hariri et al. |
| 2004/0057938 A1 | 3/2004 | Ghinelli |
| 2005/0124003 A1 | 6/2005 | Atala et al. |
| 2005/0287547 A1 | 12/2005 | Seligman |
| 2007/0020225 A1 | 1/2007 | Abramson et al. |
| 2007/0116684 A1 | 5/2007 | Atala et al. |
| 2008/0286378 A1 | 11/2008 | Behren |
| 2009/0004160 A1 | 1/2009 | Park et al. |
| 2009/0098214 A1 | 4/2009 | Nanbu et al. |
| 2010/0272782 A1 | 10/2010 | Owens et al. |
| 2011/0243999 A1 | 10/2011 | Dellamary et al. |
| 2012/0128638 A1 | 5/2012 | Gaussin et al. |
| 2012/0189586 A1 | 7/2012 | Harrell |
| 2012/0315259 A1 | 12/2012 | Friedlander |
| 2012/0321719 A1 | 12/2012 | McDonnell et al. |
| 2013/0095061 A1 | 4/2013 | Cohen et al. |
| 2013/0115197 A1 | 5/2013 | Emig et al. |
| 2013/0267008 A1 | 10/2013 | Shon et al. |
| 2013/0280344 A1 | 10/2013 | Tseng et al. |
| 2013/0280801 A1 | 10/2013 | Sun |
| 2013/0344037 A1 | 12/2013 | Edinger et al. |
| 2014/0050788 A1 | 2/2014 | Daniel et al. |
| 2014/0255357 A1 | 9/2014 | Burt |
| 2014/0255496 A1 | 9/2014 | Daniel et al. |
| 2014/0271776 A1 | 9/2014 | Vines et al. |
| 2014/0295554 A1 | 10/2014 | Kim et al. |
| 2015/0216912 A1 | 8/2015 | Koob |

\* cited by examiner

FROZEN THERAPEUTIC DOSE AND PACKAGE

CROSS REFERENCE TO RELATED APPLICATION

This application is a continuation in part of application no. PCT/US2015/035749, filed on Jun. 15, 2015 and currently pending, which claims the benefit and priority to U.S. provisional patent application No. 62/012,396, filed on Jun. 15, 2014 both entitled Frozen Therapeutic Dose and Package; this application is also a continuation in part of PCT/US2015/035746, filed on Jun. 15, 2015, which claims the benefit U.S. patent application Ser. No. 14/593,415, filed on Jan. 9, 2015 and issued as U.S. Pat. No. 9,132,156 on Nov. 15, 2015, which claims the benefit of U.S. provisional patent application No. 62/012,394, filed on Jun. 15, 2014; this application is also a continuation in part of U.S. patent application Ser. No. 14/853,889, filed on Sep. 14, 2015 and currently pending, which is a continuation in part of application Ser. No. 14/593,415, filed on Jan. 9, 2015 and issued as U.S. Pat. No. 9,132,156 on Nov. 15, 2015, and U.S. patent application Ser. No. 14/853,889 is a continuation in part of PCT/US2015/019294, filed on Mar. 6, 2015, a continuation in part of PCT/US2015/019318 filed on Mar. 6, 2015, and a continuation in part of PCT/US2015/019311, filed on Mar. 6, 2015; the entirety of each application listed above is hereby incorporated by reference herein.

BACKGROUND OF THE INVENTION

Field of the Invention

The present invention relates to a frozen therapeutic dose comprising an amniotic material including amniotic tissue and/or amniotic fluid and packaging for said dose. In an exemplary embodiment, a frozen therapeutic dose comprises live amniotic cells which may include stem cells.

BACKGROUND

Therapeutic compositions comprising amniotic fluid, tissue, and in particular amniotic stem cells are being used to treat a wide variety of conditions and ailments. Active or live stem cells are critically important in the treatment of some conditions and patients have to visit a doctor's office to receive these treatments. Some conditions require the regular application, or injection of therapeutic compositions comprising amniotic stem cells which requires the patient to make frequent visits to the doctor's office. This is inconvenient and in some cases impractical, especially when a dose of an amniotic stem cell therapeutic composition is required multiple times a day.

Amniotic stem cells are somewhat fragile and can become damaged or undergo cell death for any number of reasons including exposure to chemicals, exposure to excessive heat or simply time.

SUMMARY OF THE INVENTION

The invention is directed to a frozen therapeutic dose comprising an amniotic material and packaging for said dose. Any of the therapeutic compositions described in U.S. provisional patent application No. 61/949,087, filed on Mar. 30, 2014 and entitled Therapeutic Compositions and Methods of Use, or U.S. provisional patent application No. 62/012,394, filed on Jun. 15, 2014 and entitled Acellular Amnion Derived Therapeutic Composition, may be configured as a frozen therapeutic dose, as described herein, and both of these references are incorporated by reference herein in their entirety. In an exemplary embodiment, a frozen therapeutic dose comprises live amniotic cells which may include amniotic stem cells. A frozen therapeutic dose may be provided in a form, such as a multi-pack form, to enable a person to administer a dose to a treatment location without the need of traveling to a doctor's office or clinic. A frozen therapeutic dose package may be kept in a conventional freezer at $-20°$ C., for example, for extended periods of time and a person may remove the package as needed for treatment. Many conditions may require the administering of a therapeutic dose every day, multiple times a day, or unpredictably and traveling to a treatment location may often not be practical for an individual. In addition, there are circumstances when medical treatment may be required in remote areas, where medical attention is not readily available. For example, soldiers in the field may require treatment quickly and a frozen dose, as described herein, may be utilized in these situations. A soldier may require application of one or more doses to an injury.

A frozen dose may keep the amnion material and in particular the live amniotic cells viable for extended periods of time. Live amniotic cells, including stem cells, may remain live and viable even after being frozen for certain periods of time. A cryoprotectant may be required in some cases to protect the amnion material and in particular to preserver the viability of the amniotic stem cells. Any suitable type of cryoprotectant may be used including, but not limited to, glycols, ethylene glycol, propylene glycol, glycerol, 2-methyl-2,4-pentanediol (MPD), alcohols, dimethyl sulfoxide (DMSO), sugars, polyols, glucose and the like. Some of the cryoprotectants may raise the pH and a buffer may be needed to reduce this elevated pH prior to administering to a treatment location.

In an exemplary embodiment, additional cells may be added to a frozen dose composition, such as cells from a stromal vascular fraction, bone marrow or cells from any other tissue. These cells may be stem cells. In addition, these cells may be viable cells that are frozen and be viable upon thawing or administering of the frozen dose.

A therapeutic dose, as used herein comprises amniotic material including, but not limited to, amniotic membrane, amniotic fluid, amniotic cells, amniotic stem cells and/or cytokines, collagen, proteins, and growth factors derived from amnion material. In an exemplary embodiment, a frozen therapeutic dose comprises live amniotic stem cells. A therapeutic dose may also comprise a diluent, a cryoprotectant, a buffer or other materials configured to enhance the effectiveness of the treatment. In one embodiment, a therapeutic dose comprises amnion material and a buffer to reduce the Ph of a cryoprotectant. In another embodiment, a therapeutic does comprises anti-inflammatory nano-particles and/or statins, HMG-CoA reductase inhibitors to reduce inflation at a treatment location. A diluent may comprise a saline solution, water, a plasma containing solution, such as an isotonic solution from Baxter Inc. In some embodiments, it may be desired to have a viscous frozen dose upon thawing or melting. It may be desirable to slow the absorption of the frozen dose into a treatment location. A hydrogel may be used as a diluent and may provide for a high viscosity thawed frozen dose, and may prolong the time the therapeutic frozen dose is in contact with a treatment location. Any suitable type of hydrogel may be combined with the therapeutic composition.

In an exemplary embodiment, a therapeutic dose comprises a concentration of live amniotic cells, which may include or consist essentially of at least about $0.01\times10^6$ cells/ml or more, $0.1\times10^6$ cells/ml or more, $0.5\times10^6$ cell/ml or more, about $1\times10^6$ cells/ml or more, about $2\times10^6$ cells/ml or more and any range between and including the values provided. In some applications, a higher concentration of amniotic cells may provide a more rapid and better therapeutic effect. In one embodiment, amniotic stem cells are concentrated in the therapeutic dose, whereby the concentration is substantially higher than an initial concentration before processing.

A frozen therapeutic dose may be configured in a dosing package having a dose compartment and a compartment closure. An individual dosing package may be relatively small, such as no more than about 100 ml, no more than about 50 ml, no more than about 25 ml, no more than about 10 ml, no more than about 5 ml, from out 0.01 ml to 5 ml, and any range between and including the volumes provided. In an exemplary embodiment, a frozen therapeutic dose is provided in a detachable dosing package that is part of a multi-dose pack. For example, two or more detachable dosing packages may be coupled together in a multi-dose pack and a separation feature, such as perforations, may be used for detachment. Any number of detachable dosing packages may be configured in a multi-dose pack including more than three, more than five, more than ten, more than twenty and the like.

A dosing package may comprise a frozen therapeutic dose and a secondary material within a single compartment whereby the frozen materials are substantially separate and will not mix until they thaw. For example, a frozen therapeutic dose of amniotic stem cells may be frozen and a cryoprotectant may be added to ensure that the stem cell are live upon thawing. The cryoprotectant may be an irritant for some treatment locations, such as the eye, and therefore a buffer or buffer solution is added to the dosing package compartment in a frozen state. The two solid materials within the dosing package compartment will stay substantially separate and will not mix until the contents of the compartment are thawed. In this way, the therapeutic dose applied to a treatment location will not be irritating. A secondary material may be configured within a single dose compartment including, but not limited to, a diluent, a buffer, a secondary therapeutic composition and the like.

In another embodiment, a secondary material or component of a therapeutic dose is provided in a separate compartment, whereby the contents of the secondary compartment are added to the frozen dose before application to a treatment location. A set of compartments, one with a frozen therapeutic dose of amnion material, and another compartment with a secondary material including, but not limited to, a diluent, a buffer, a secondary therapeutic composition and the like, may be coupled together. A multi-dose pack may comprise a separation feature that is configured to detach the two compartments. A secondary therapeutic composition, may comprise amnion material and may have a different composition than a first therapeutic composition.

A frozen dose may be configured to be removed from a dose compartment and placed directly onto a treatment location. For example, a frozen dose pellet may be removed from a dose compartment and placed on the eye or under an eyelid. In another embodiment, a frozen dose may be placed in an applicator, such as a dropper, spray bottle, or syringe for example. A diluent, buffer or other secondary material may be added to an applicator. A frozen dose may be allowed to thaw prior to application to a treatment location, or melt in a secondary material.

In another embodiment, a frozen therapeutic dose is coupled with a compartment closure, whereby the compartment closure can be removed from the compartment and the therapeutic dose applied to a treatment location. For example, a frozen dose may be configured in a blister pack having a peel off compartment closure. The frozen dose may be attached to the peel way compartment closure whereby upon removal of the closure it can be applied directly to a treatment location, such as the skin, eye, mouth, etc. In another embodiment, a frozen dose is attached to a closure cap and upon removal can be swabbed over a treatment area, or placed in or on the mouth.

In still another embodiment, a frozen dose is configured in a dose package applicator comprising a compartment closure and at least one opening in a compartment cover. In this embodiment, the compartment closure, such as a foil sheet, can be removed to expose the compartment cover having at least one opening therein. The dose package applicator can be placed directly on a treatment location and the compartment can be pressed to enable the therapeutic composition to pass through the opening. In another embodiment, a compartment cover may be a porous material that enables the therapeutic composition to transfer therethrough as it thaws.

The therapeutic composition may also be administered by a syringe or transcatheter. A frozen dose may be removed from a dose package and then drawn into a syringe. The syringe may then be used to inject the therapeutic composition to any suitable treatment location.

A therapeutic composition may be applied to a treatment location by topical application, ingestion, injection, transcatheter and the like. In addition, some conditions may require some combination of the application methods described herein.

A therapeutic composition may be applied to any suitable treatment location including, but not limited to, topically to the exterior of the body including the skin, a wound, a scare, a wrinkle and the like, to the digestive system by ingestion or injection, to an organ by injection or by direct application during surgery, for example.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1A:
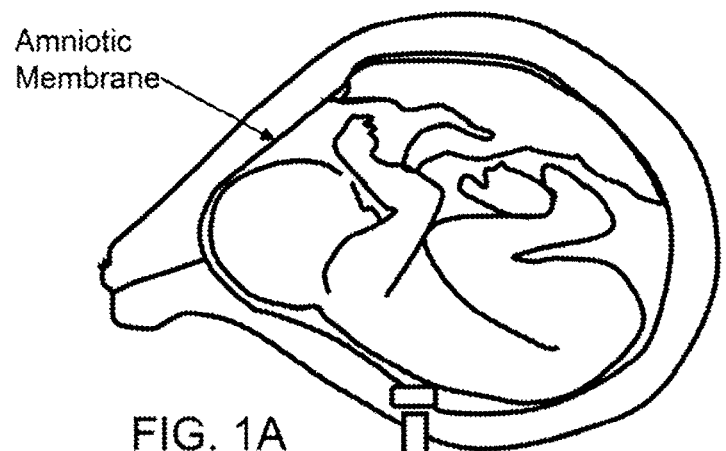

FIG. 1A shows a cross-sectional diagram of amniotic membrane surrounding a fetus in utero.

Figure 1B:
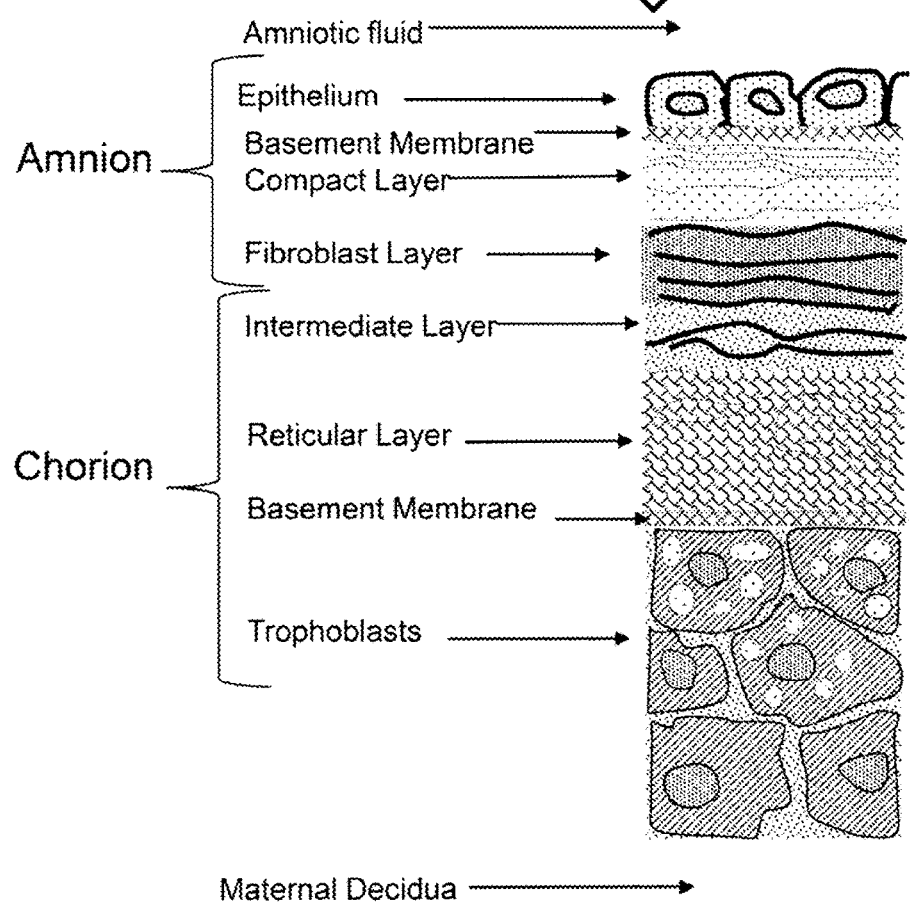

FIG. 1B shows a cross-section diagram of the layers of the amnion and chorion.

Figure 2A:
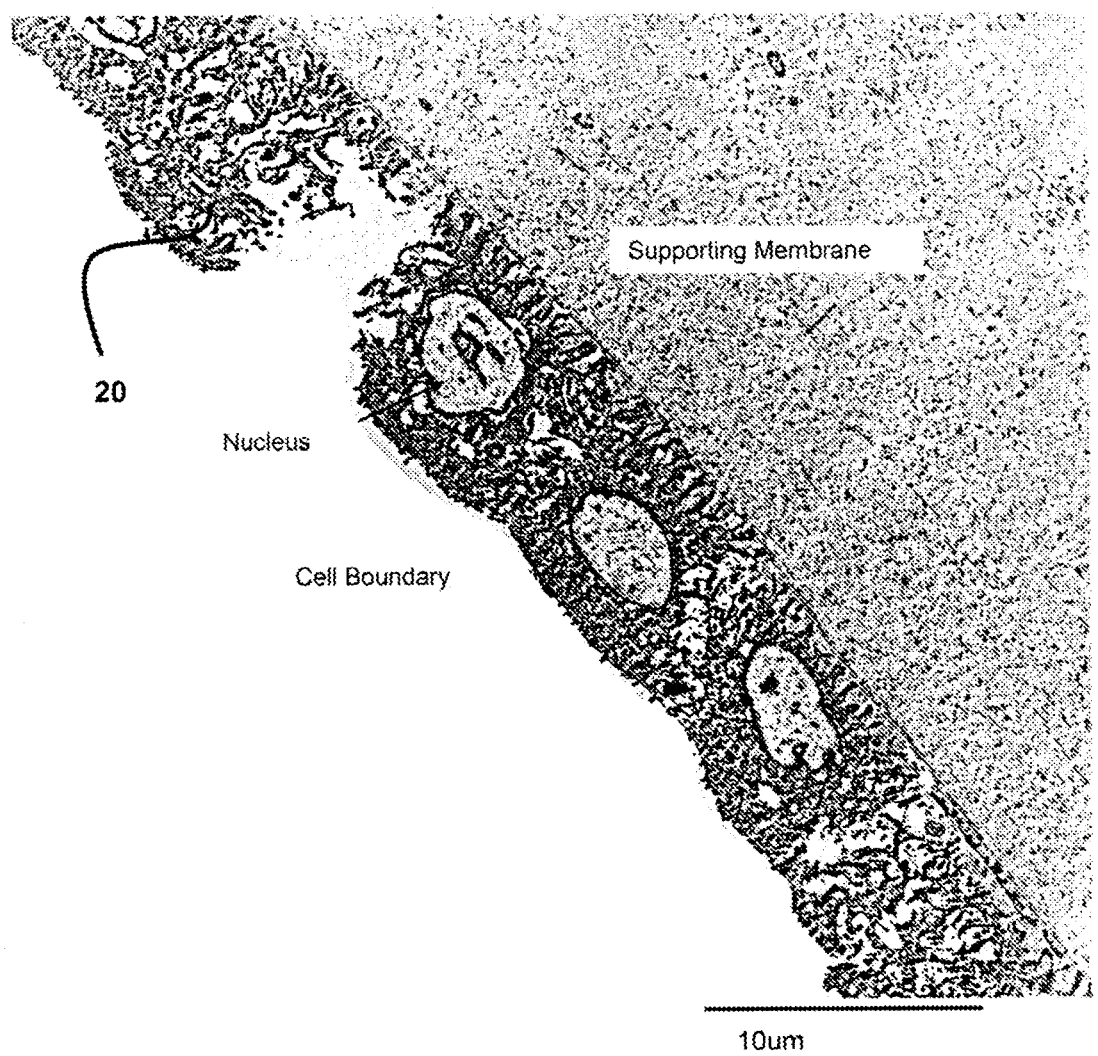

FIG. 2A show a transmission electron micrograph (TEM) of the epithelium layer of the amniotic membrane having a single layer of amniotic stem cells. The TEM was taken at 2500× magnification.

Figure 2B:
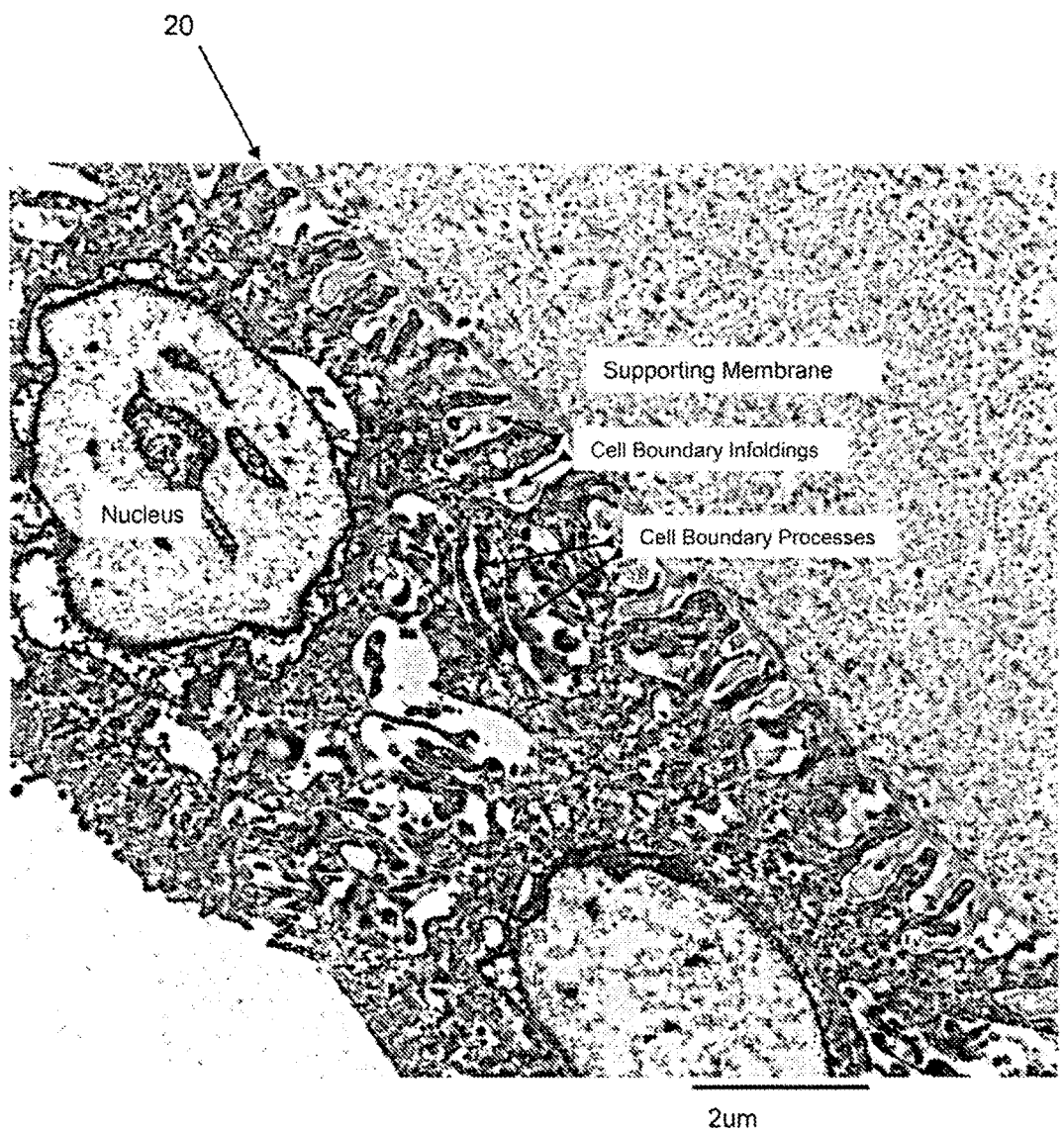

FIG. 2B show a TEM of the epithelium layer of the amniotic membrane having a single layer of amniotic stem cells. The TEM is at 8200× magnification.

Figure 3A:
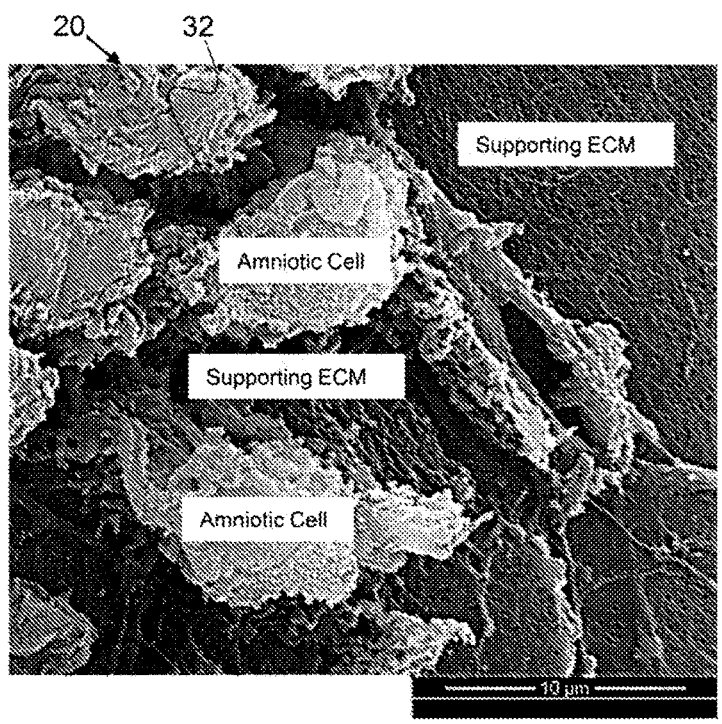
Figure 3B:
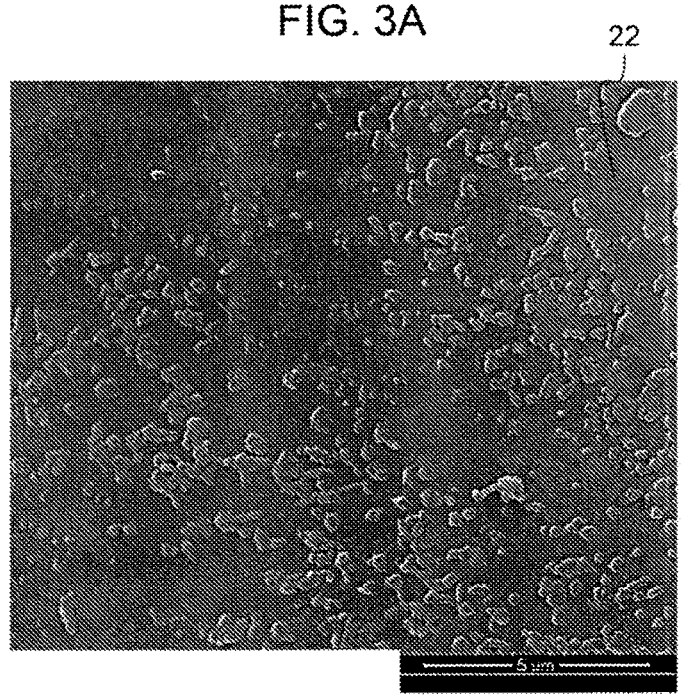

FIG. 3A is a scanning electron micrograph (SEM) of an amniotic membrane having amniotic cells FIG. 3B is a SEM of cryo-fractured amniotic membrane particles.

Figure 4A:
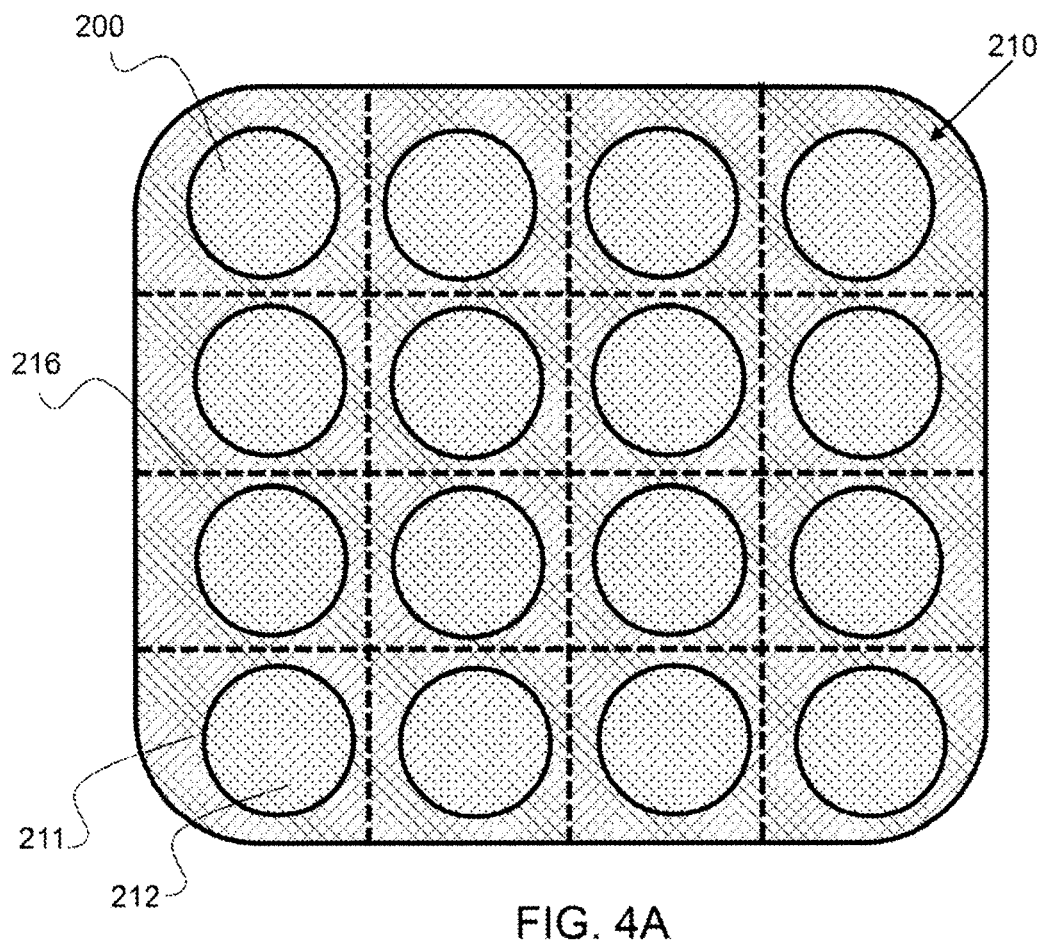

FIG. 4A shows a top down view an exemplary multi-dose pack having a plurality of frozen doses.

Figure 4B:
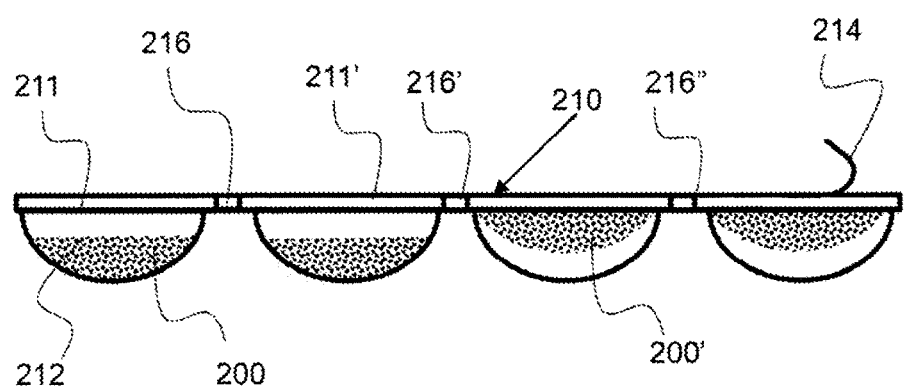

FIG. 4B shows a side view of an exemplary multi-dose pack have a plurality of frozen doses.

Figure 5:
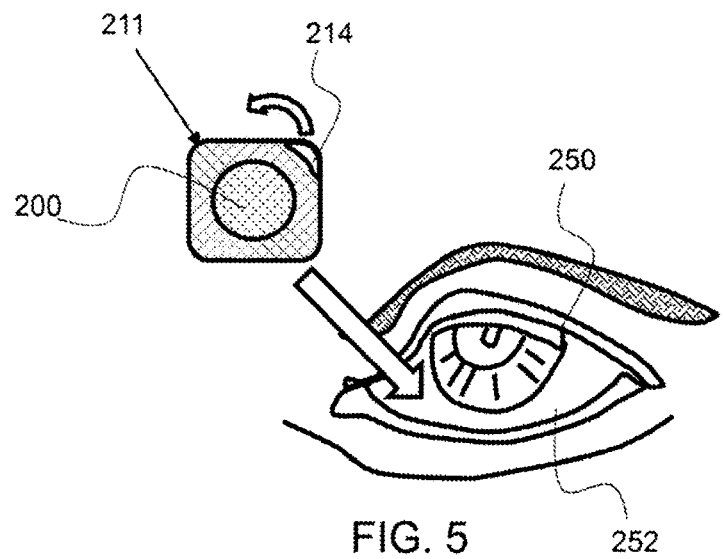

FIG. 5 shows an exemplary detached dosing package being opened for placement in an eye.

Figure 6:
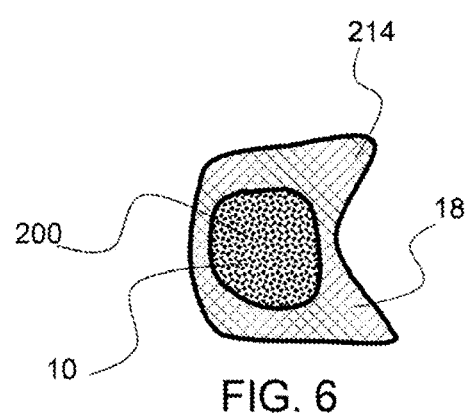

FIG. 6 shows an exemplary compartment closure having a frozen dose attached thereto.

Figure 7:
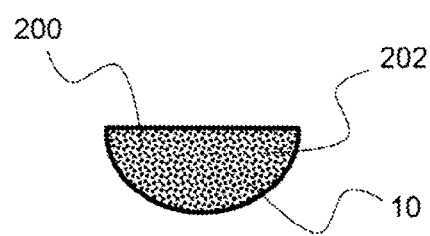

FIG. 7 shows an exemplary frozen dose.

Figures 8A, 8B:
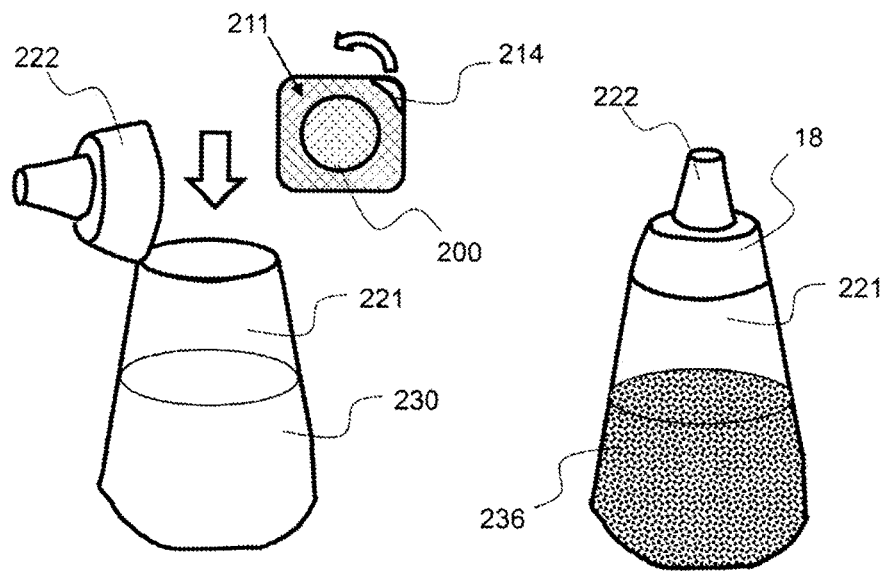

FIG. 8A shows an exemplary frozen dose being placed into a dropper applicator with a diluent configured therein. FIG. 8B shows the dropper applicator with the frozen therapeutic dose melted and dispersed therein.

Figure 9:
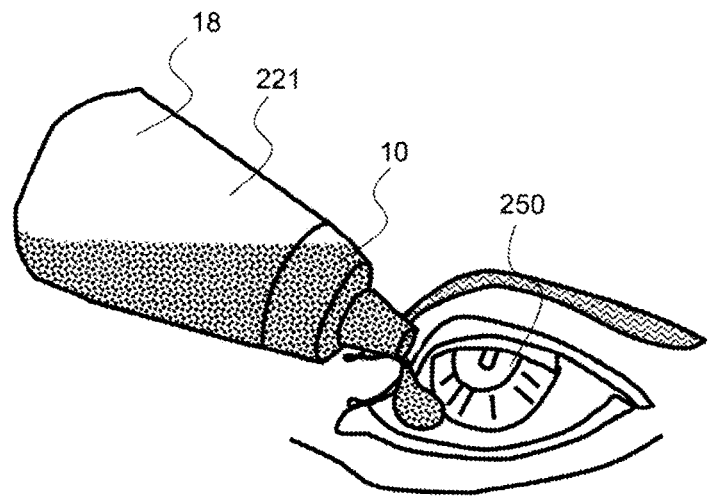

FIG. 9 shows an exemplary dropper applicator being used to administer a drop of therapeutic composition into an eye.

Figure 10A:
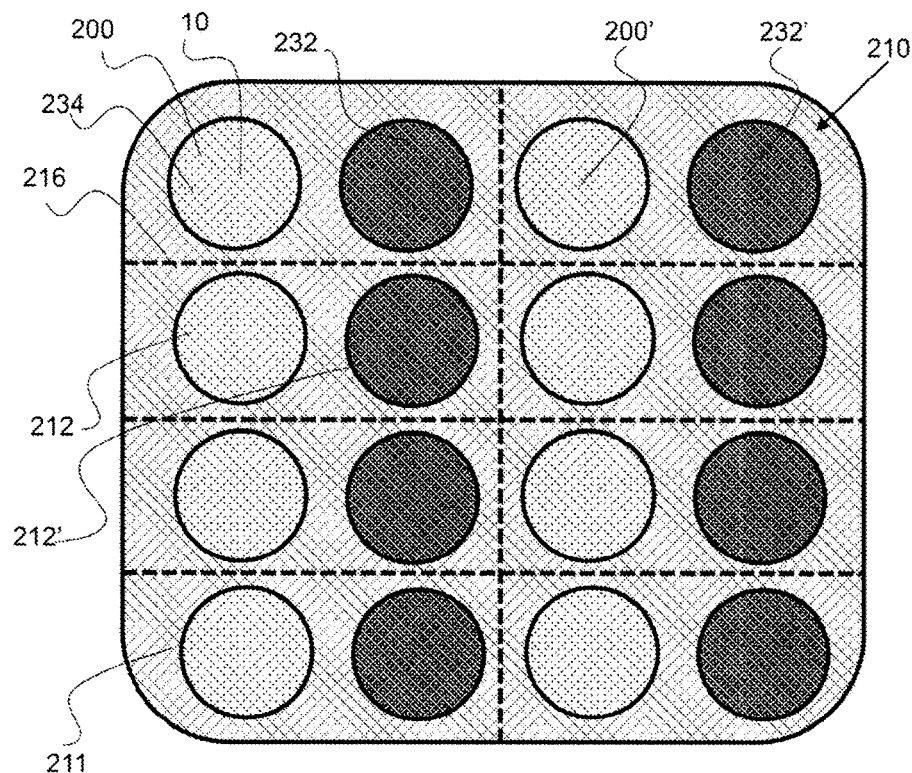

FIG. 10A shows a top down view an exemplary multi-dose pack having a plurality of frozen doses wherein a set of compartments are configured to be detached from the multi-dose pack.

Figure 10B:
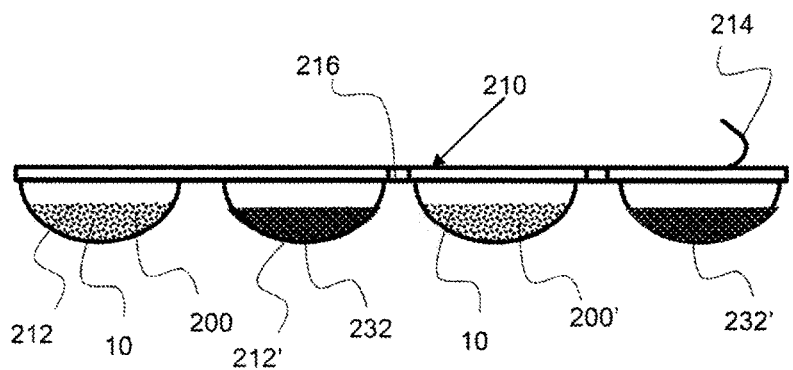

FIG. 10B shows a side view of an exemplary multi-dose pack, wherein each set of compartments contains a frozen therapeutic dose in a first compartment and a buffer in a second compartment.

Figure 11:
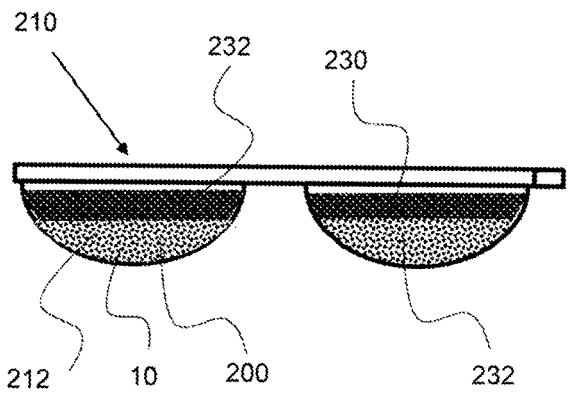

FIG. 11 shows a side view an exemplary multi-dose pack, wherein each compartment comprises a frozen therapeutic dose that is substantially separated from a buffer.

Figure 12:
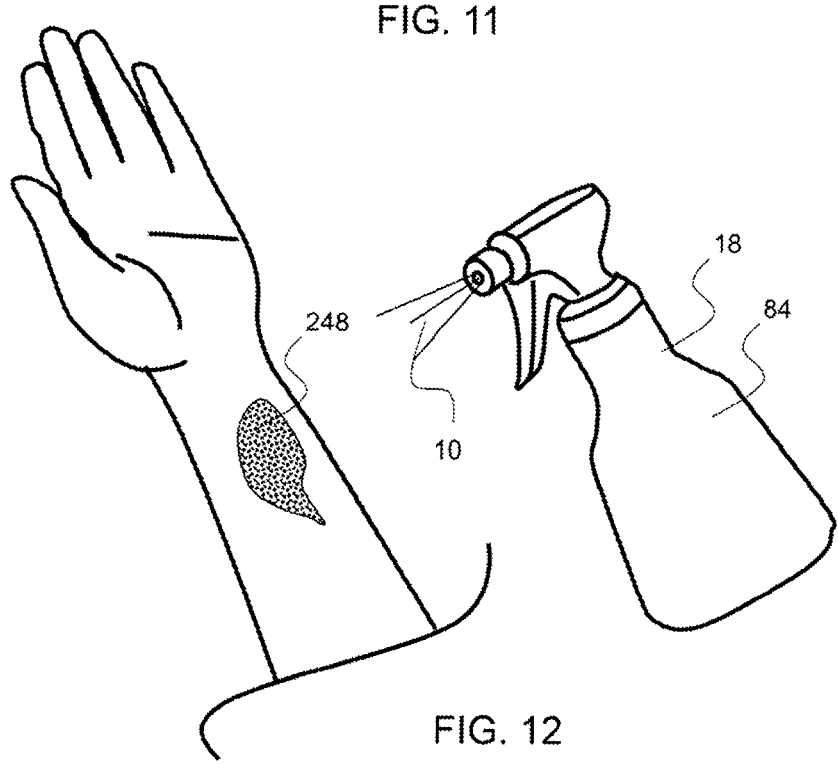

FIG. 12 shows an exemplary spray bottle administering a therapeutic composition to an affected area of the skin.

Figure 13:
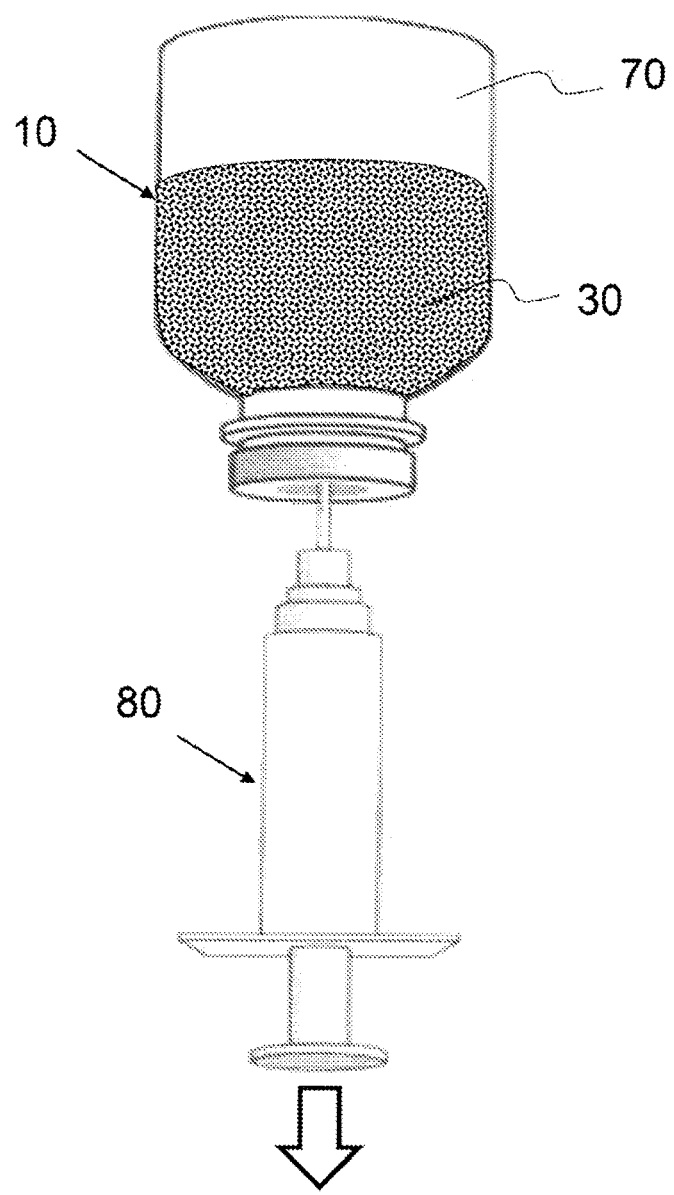

FIG. 13 shows an exemplary syringe applicator drawing a therapeutic dose into the syringe.

Figure 14:
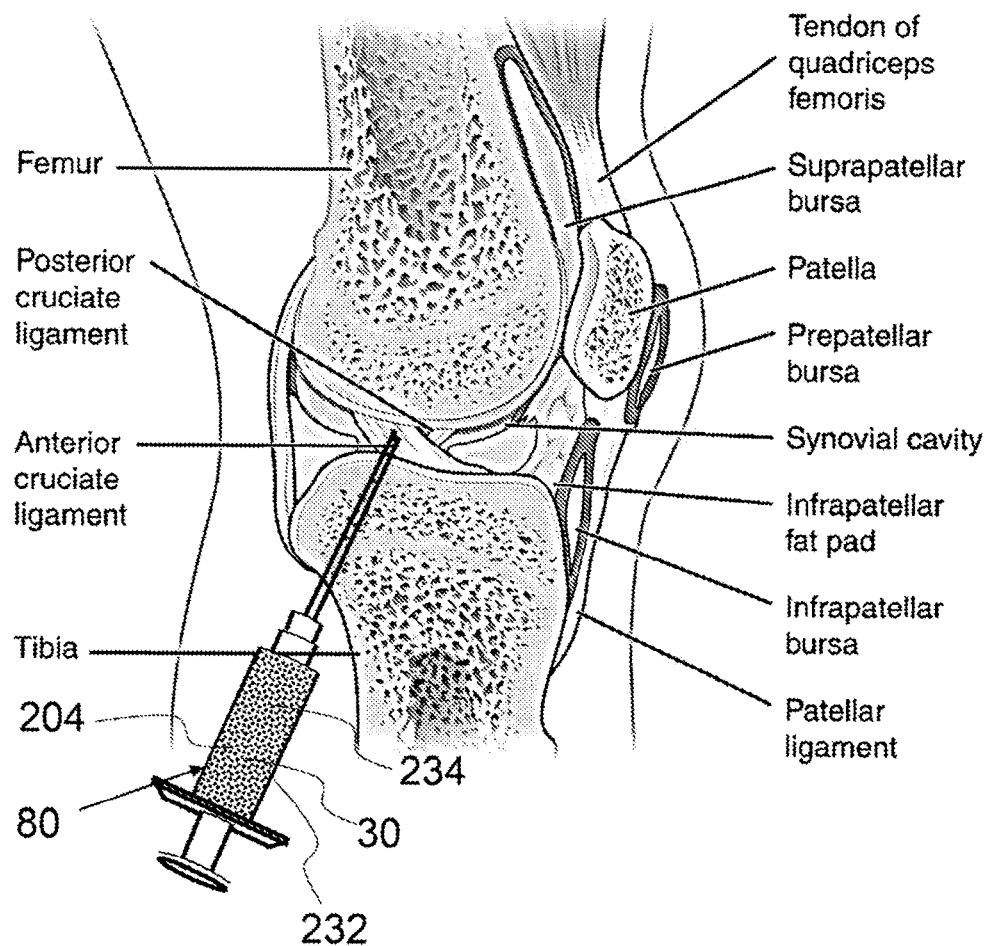

FIG. 14 shows an exemplary syringe applicator administering a therapeutic dose into an affected area by injection.

Figure 15:
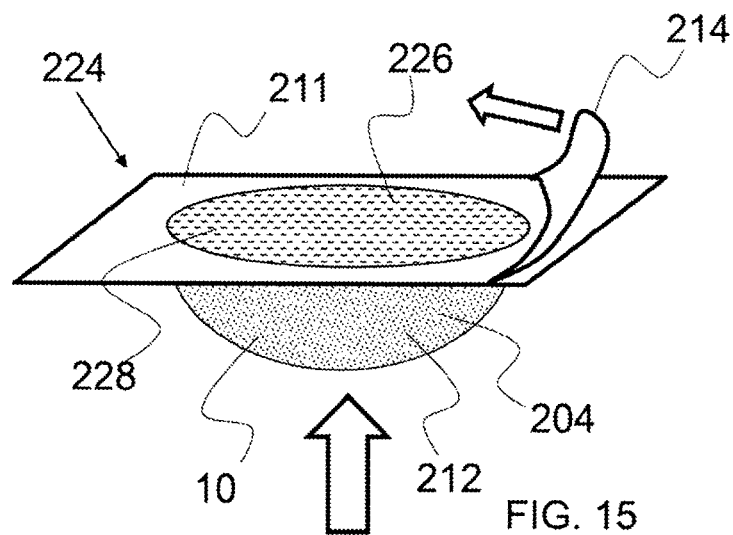

FIG. 15 shows an isometric view of a dose package applicator.

Figure 16:
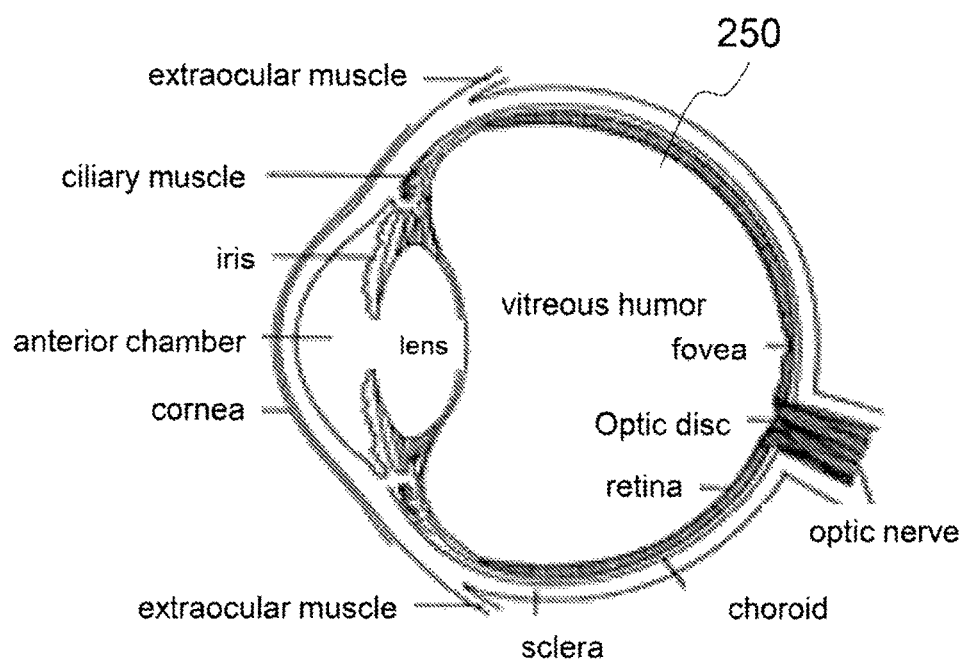

FIG. 16 shows a diagram of the eye and some of the parts of the eye that may be affected areas for treatment with a therapeutic dose.

Figure 17:
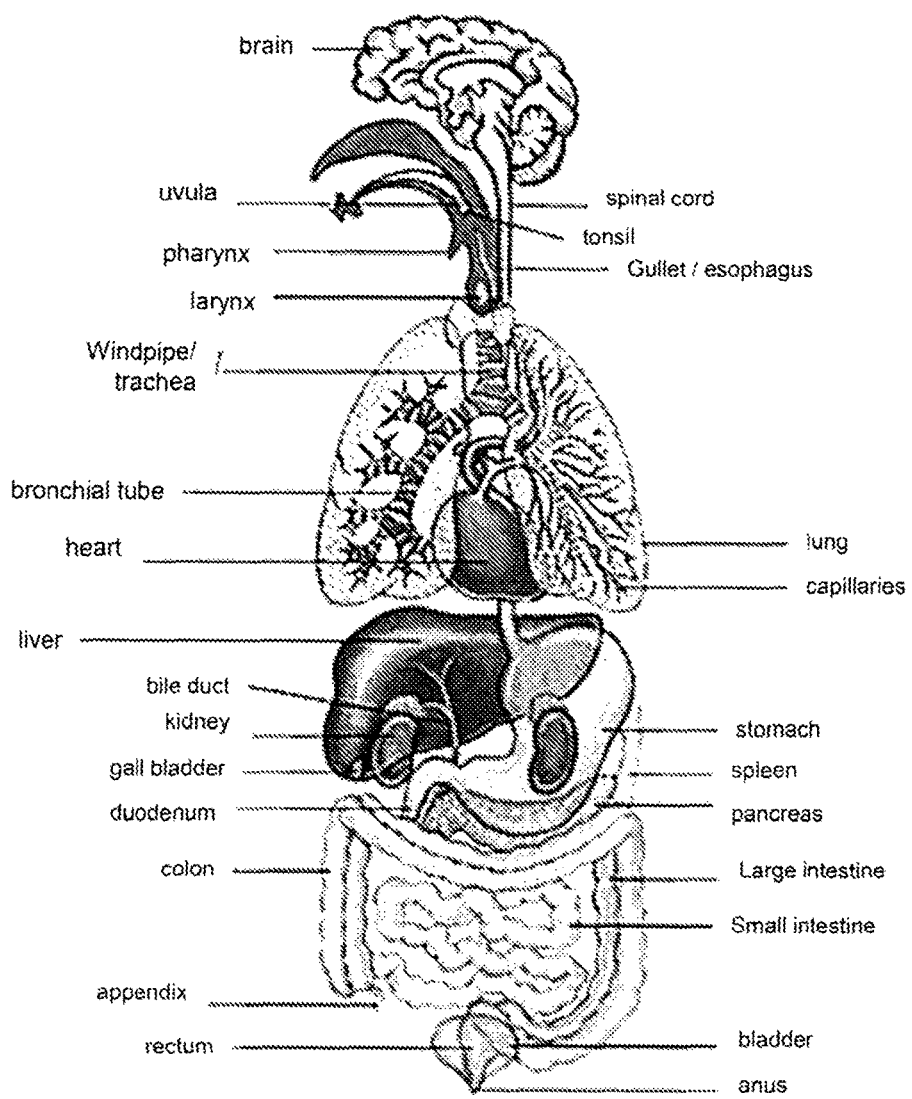

FIG. 17 shows a diagram of the some of the organs within the body that may be an affected area for treatment with a therapeutic dose.

Figure 18:
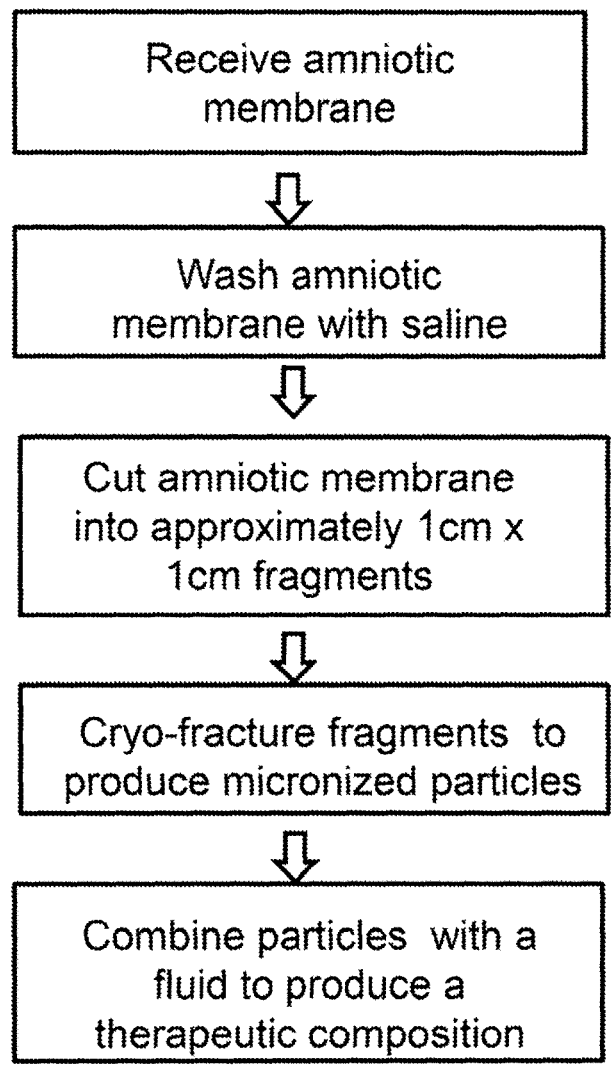

FIG. 18 shows a diagram of a process to produce a therapeutic composition comprising micronized amniotic membrane particles Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown if FIG. 1A the amniotic membrane surround a fetus in utero. As shown in FIG. 1B, the amniotic membrane comprises an amnion portion and a chorion portion. As described herein, the amnion portion may be separated from the chorion. In an exemplary embodiment, the epithelium, or inner most layer of the amniotic membrane is removed and used to produce particles for the therapeutic composition, as described herein. The particles may consist essentially of the epithelium, consists essentially of the epithelium and base membrane, consist essentially of the epithelium, base membrane and compact layer, or consist essentially of epithelium, base membrane, compact layer, and fibroblast layer.

As shown in FIGS. 2A and 2B, the epithelium layer of the amniotic membrane has a single layer of amniotic stem cells. The tissue around the amniotic stem cells may protect and enhance the viability of these stem cells when the epithelium is cryo-fractured to produce particles for the therapeutic composition.

A s shown in FIG. 3A, an amniotic membrane 20 comprises a plurality of amniotic cells 32.

As shown in FIG. 3B, particles of cryo-fractured amniotic membrane particles are on the order of 0.2 to 0.5 μm in size. The average particle size shown is less than 2 μm. There are no particles shown that are larger than 2 μm and substantially all of the particles are less than 1 μm in size. The SEM shows that the micronized amniotic membrane particles are irregularly shaped. As shown, some of the particles have a planar surface.

As shown in FIG. 4A, an exemplary multi-dose pack 210 has a plurality of frozen doses 200. The multi-dose pack 210 comprises a plurality of detachable dosing packages 211 and a separating feature 216, such as perforations. The separating feature may be configured for the detachment of individual detachable dose packages or two or more detachable dose packages.

As shown in FIG. 4B, an exemplary multi-dose pack 210 has a plurality of frozen doses 200 in dose compartments. The individual doses are contained with discrete compartments 212 and a compartment closure 214 is configured over the compartments. The compartment closure 214 is shown being peeled away from the dose pack. Some of the doses 210 are shown configured in the bottom of the compartment 212 and some of the dose 200' are shown being attached to the compartment closure 214. A separating feature 216 is configured between each of the detachable dose packages.

As shown in FIG. 5, an exemplary detached dosing package 211 is being opened for placement of a frozen dose 200 in an eye 250. The dose may be placed directly into the eye or under the eyelid 252. In addition, a user may separate an individual detachable dose package from a multi-dose pack, allow the frozen dose configured therein to melt, and then administer to an affected area, such as the eye.

As shown in FIG. 6, an exemplary compartment closure 214 has a frozen dose 200 attached thereto. In this embodiment, the compartment closure may be removed from a dosing package 211 and placed onto an affected area with the frozen dose attached. The compartment closure 214 is used as an applicator 18 in this embodiment. After the dose has dissolved, the compartment closure may be removed from the affected area, such as an eye. This embodiment allows for safe application of the dose to an affected area with minimal handling.

As shown in FIG. 7, an exemplary frozen dose 200 comprises a therapeutic composition 10. The frozen dose pellet 202 has a partial spherical shape as it conformed to the compartment in which it was provided. As described herein, the frozen therapeutic dose comprises amnion material. In addition, a secondary therapeutic material and/or diluent, cryoprotectant and/or buffer may be configured within a single frozen dose pellet. Any suitable shape and size of frozen dose pellet may be configured for application to a specific treatment location. For example, a thin planar sheet frozen dose may be used for application to the skin such as a wound or scar. In another embodiment, a pellet with rounded surface may be configured for placement under an eyelid, to reduce any discomfort.

As shown in FIG. 8A, an exemplary frozen dose 200 is being placed into a dropper applicator 221 with a diluent 230 configured therein. The applicator cap 222 is open and the compartment closure 214 is being peeled off to drop the frozen dose pellet 202 into the dropper. FIG. 8B shows the dropper applicator 221 with a diluted frozen therapeutic dose 236 therein.

As shown in FIG. 9, an exemplary dropper applicator 221 is being used to administer a drop of therapeutic composition 10 into an eye 250.

As shown in FIG. 10A, an exemplary multi-dose pack 210 has a plurality of frozen doses 200 and buffers configured in sets of compartments. A separation feature 216 is configured to enable the detachment of a frozen dose compartment 212 and a buffer compartment 212', or compartment set. In this embodiment, a frozen dose comprises a therapeutic composition 10 and a cyroprotectant. The cryoprotectant may cause the frozen dose to have high pH and may irritate affected areas. The buffer 232 may be configured to mix with the frozen dose upon thawing and reduce the pH prior to administering the mixture to an affected area or treatment location. It is to be understood that a second compartment of a compartment set may comprise a secondary therapeutic composition of different composition, a therapeutic composition that does not comprise amnion material, an a cellular amnion derived therapeutic composition, a composition enhancer, an anti-inflammatory, a diluent and the like.

As shown in FIG. 10B, an exemplary multi-dose pack 210, comprises sets of compartments having a frozen therapeutic dose 200 in a first compartment 212 and a buffer 232 in a second compartment 212'.

As shown in FIG. 11, an exemplary multi-dose pack 210 comprises a frozen therapeutic dose 200 that is substantially separated from a buffer 232 in dose compartment 212 and a frozen therapeutic dose 200 that is substantially separated from a diluent 230 as shown in the dose compartment 212'. In this embodiment, a therapeutic composition may be frozen separately from a buffer or diluent whereby they are configured in the dose compartment in a frozen state and substantially separate from each other. The concentration of the frozen dose and secondary material, such as diluent, buffer, or secondary therapeutic composition may remain substantially different while maintained in a frozen state. In this manner, the single dose compartment 212 may be opened and place onto a treatment location or the contents of the compartment may be allowed to thaw, whereby the contents will mix prior to administering to a treatment location.

As shown in FIG. 12, an exemplary spray bottle 84 type applicator 18 is administering a therapeutic composition 10 to an affected area or treatment location 248 of the skin.

As shown in FIG. 13, an exemplary syringe 80 applicator is drawing a therapeutic composition 10 into the syringe. The therapeutic composition 10 within the enclosure 70 comprises live amniotic stem cells 30. The therapeutic composition may also comprise a diluent and a frozen dose may have been thawed in the diluent.

As shown in FIG. 14, an exemplary syringe 80 applicator is administering a therapeutic dose 204 into an affected area by injection. The therapeutic dose is a composition derived from thawing a frozen dose, as described herein and comprises live amniotic stem cells 30, a cryoprotectant 234 and a buffer 232. The therapeutic dose is being injected into a joint.

As shown in FIG. 15, a dose package applicator comprises a dose compartment 212 with a therapeutic composition 10 therein. The dose package applicator may be one of a plurality of individual dose package applicators couple together in a multi-dose pack. The dose package applicator 224 comprises a compartment closure 214 that is being peel off to expose openings 226 in a compartment cover portion 228. A compartment cover portion may be a portion of a detachable dosing package and may be a sheet of plastic material, for example. The compartment cover portion comprises opening 226 to allow the administering of the therapeutic dose 204 by pressing on the dose compartment, as indicated by the arrow pointing up. The therapeutic dose 204 is squeezed through the opening an onto a treatment location. It is to be understood that a frozen dose package with a compartment cover having at least one opening may be configured for placement onto a treatment location to allow the frozen dose to transfer through the opening as the frozen dose thaws and melts.

FIG. 16 shows a diagram of an eye 250 and some of the parts of the eye that may be treatment locations for treatment with a therapeutic dose derived from a frozen dose, as described herein. For example, a therapeutic composition, as described herein, may be applied topically and/or injected into the iris, anterior chamber, lens, vitreous humor, ciliary muscle, cornea, extraocular muscle, sciera, choroid, retina and the like.

FIG. 17 shows a diagram of the some of the organs within the body that may be an affected area for treatment with a therapeutic dose derived from a frozen dose, as described herein. A therapeutic composition, as described herein, may be introduced into any anatomy shown in FIG. 17 by direct injection, topical application, or transcatheter.

FIG. 18 shows a diagram of a process to produce a therapeutic composition comprising micronized amniotic membrane particles. As shown, an exemplary process to produce a therapeutic composition, as described herein, comprises the steps of cryo-fracturing amniotic membrane fragments to produce micronized amniotic membrane particles. As described, the amniotic membrane fragments may be cryo-fractured with a blunt object, such as a bar, that reduces shear and damage to the particles. In a preferred embodiment, the fragments are cryo-fractured with an object having substantially no sharp edges. The micronized particles are combined with any suitable carrier fluid to produce a therapeutic composition. In an exemplary embodiment, the micronized particles are dispersed in a fluid comprising amniotic fluid and amniotic stem cells. In another embodiment, the micronized particles are dispersed in a concentrated amniotic stem cell fluid.

Definitions

Amnion material, as used herein, includes amniotic membrane, amniotic cells including amniotic stem cells, amniotic fluid, and/or cytokines, collagen, proteins and growth factors derived from amnion or amniotic fluid.

Treatment location and affected area are used interchangeable through the specification.

A therapeutic dose, as used herein, comprises a frozen therapeutic dose comprising amnion material, and may be thawed and combined with secondary material, such as buffer, diluent, a secondary therapeutic composition and the like.

A cryoprotectant is a substance used to protect biological tissue from freezing damage from ice formation, for example.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A therapeutic dose package, comprising a plurality of individual compartments coupled together in a multi-dose pack comprising:
   a frozen therapeutic dose comprising a therapeutic composition comprising:
      acellular amniotic membrane particles;
      a carrier fluid comprising an acellular amniotic fluid;
   wherein the acellular amniotic membrane particles consist essentially of micronized amniotic membrane; and
   wherein the therapeutic composition is essentially free of any viable amniotic membrane cells or viable amniotic fluid cells; and
   wherein the plurality of individual compartments are detachably attached together.

2. The therapeutic dose package of claim 1, wherein the frozen therapeutic dose has a volume of no more than about 40 ml.

3. The therapeutic dose package of claim 1 wherein the frozen therapeutic dose further comprises a plurality of non-amnion derived cells.

4. The therapeutic dose package of claim 3, wherein the non-amnion derived cells comprise stromal vascular fraction cells.

5. The therapeutic dose package of claim 3, wherein the non-amnion derived cells comprise stem cells.

6. The therapeutic dose package of claim 1, wherein the frozen therapeutic dose comprises amnion derived materials selected from the group consisting of: cytokines, proteins, growth factors, and collagen.

7. The therapeutic dose package of claim 1, wherein the frozen therapeutic dose is a solid.

8. The therapeutic dose package of claim 1, wherein the frozen therapeutic dose further comprising a cryoprotectant, and wherein the frozen therapeutic dose is cryopreserved.

9. The therapeutic dose package of claim 8, wherein the cryoprotectant comprises DMSO.

10. The therapeutic dose package of claim 1, wherein the frozen therapeutic dose further comprises a pH buffer.

11. The therapeutic dose package of claim 1, wherein the frozen therapeutic dose further comprises a diluent.

12. The therapeutic dose package of claim 11, wherein the diluent comprises a plasma containing diluent.

13. The therapeutic dose package of claim 11, wherein the diluent comprises an anti-inflammatory.

14. The therapeutic dose package of claim 1, further comprising a frozen buffer that is configured within the compartment with the frozen therapeutic dose but is substantially separated from the frozen therapeutic dose.

15. The therapeutic dose package of claim 1, wherein the first compartment comprises said frozen therapeutic dose and a second compartment comprises a buffer.

16. The therapeutic dose package of claim 1, wherein the first compartment comprises said frozen therapeutic dose and a second compartment comprises a diluent.

* * * * *